United States Patent [19]
Burton et al.

[11] 4,269,179
[45] May 26, 1981

[54] ORTHOPEDIC GRAVITY TRACTION BRACE

[75] Inventors: Charles V. Burton, Wayzata; Wallace W. Lossing, Minneapolis, both of Minn.

[73] Assignee: Abbot-Northwestern Hospitals Inc., Minneapolis, Minn.

[21] Appl. No.: 22,712

[22] Filed: Mar. 22, 1979

Related U.S. Application Data

[63] Continuation of Ser. No. 683,276, May 5, 1976, abandoned.

[51] Int. Cl.³ .................................................. A61H 1/02
[52] U.S. Cl. ........................................... 128/75; 128/78
[58] Field of Search .............. 128/75, 84, 78, DIG. 15

[56] References Cited

U.S. PATENT DOCUMENTS

| | | | |
|---|---|---|---|
| 3,160,143 | 12/1964 | Gray | 128/75 |
| 3,167,068 | 1/1965 | Carr | 128/75 |
| 3,872,860 | 3/1975 | Noblitt | 128/75 |

*Primary Examiner*—John D. Yasko
*Attorney, Agent, or Firm*—Merchant, Gould, Smith, Edell,

[57] ABSTRACT

This is an orthopedic lumbar traction brace which is specifically designed to be attached to the lower rib cage of a patient in a manner to comfortably and safely support the patient at the desired hanging angle to provide gravity traction on the lumbar vertebra of the back, as when used in a gravity lumbar reduction system as described in the co-pending application of Charles V. Burton, M.D.

6 Claims, 5 Drawing Figures

ORTHOPEDIC GRAVITY TRACTION BRACE

This is a continuation of application Ser. No. 683,276, filed May 5, 1976, now abandoned.

Prior to applicants' invention, various types of orthopedic braces have been used for permitting traction to be applied to a patient's lumber spine area. These devices are disclosed in U.S. Patents. F. L. Gray, U.S. Pat. No. 3,160,143; Gurkin, U.S. Pat. No. 3,799,156; Beard et al, U.S. Pat. No. 3,572,327; Feldman, U.S. Pat. No. 3,797,483; Ellis, U.S. Pat. No. 3,353,532 and Carr, U.S. Pat. No. 3,167,068. None of these is satisfactory for gravity traction systems as described in a co-pending application by Charles V. Burton, M.D., nor adapted for home use for periodic treatment without hospitalization. The comfort and safety afforded the patient by providing a stretchable vest material which conforms to the contour of the patient's lower rib cage and torso portion disposed immediately therebelow are important parts of applicants' concept. Also, the ease with which the device can be put on, makes it possible for a patient to attach the brace without assistance.

The following is a description of various views in the accompanying drawings.

Figure 1:
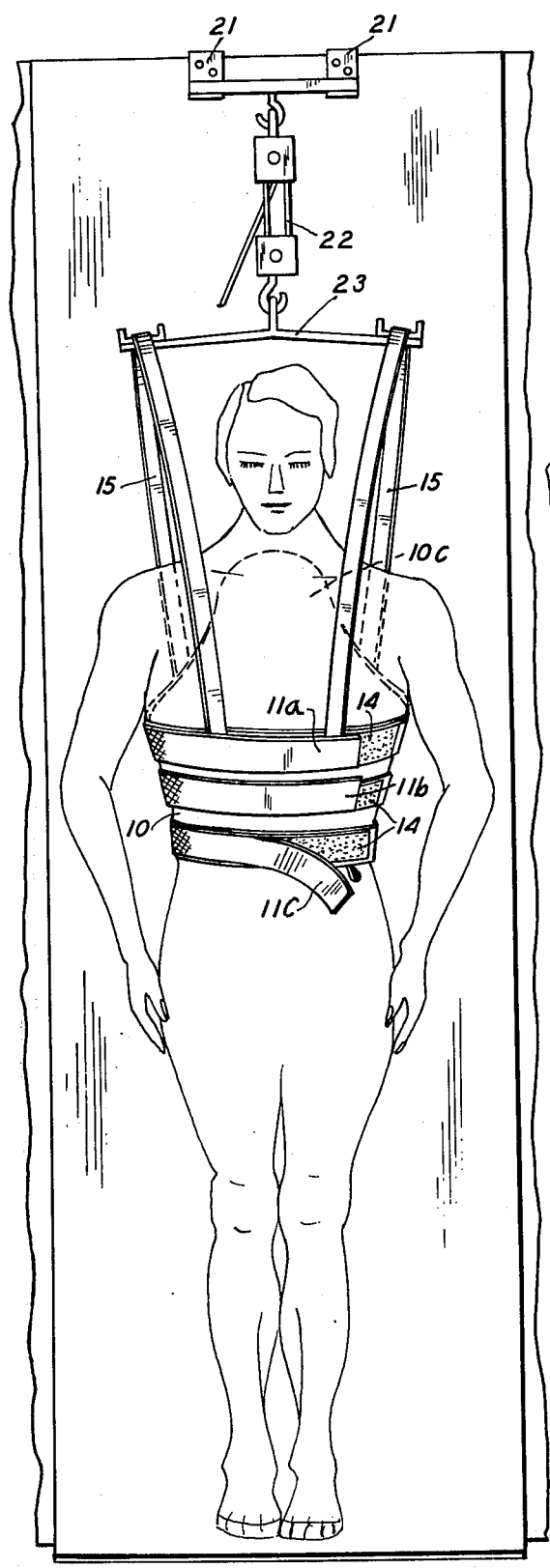
FIG. 1 is a front elevational view of a device embodying this invention being worn by a patient disposed in operative traction applying position.

The brace includes a main body vest portion 10 made from padded stretchable material such as a material known as Velfoam furnished by Smalley and Bates, Inc., Nutley, New Jersey, which has a padded foam inner lamination 10a and a felt outer lamination 10b. A plurality of circumferential straps 11a, 11b and 11c are connected at the center of the back panel 10c of the main body portion 10. In the form shown, a reinforcing tape 12, made from suitable material such as nylon webbing, is securely sewn to the center portions of straps 11a, b and c and positively secures the said straps to the lower back panel of the main body portion 10. The circumference of the main body portion 10 is adjusted to close around the body of a patient and loops 10d are provided to hold the same around the patient while the straps are being tightened.

The straps 11a, b and c are made from woven nylon webbing and have Velcro hook surfaces 13 applied to the underside thereof. The nylon Velcro straps are also furnished by said Smalley and Bates, Inc. These Velcro hook surfaces securely attach the straps to the outer felt surfaces of the body portion 10 after said body portion has been wrapped around the patient to conform to the contour of the patient's lower rib cage so that the stretchable felt-covered foam material is secured to the body of the patient in its contour-conforming relation by said straps. The straps 11a, b and c are substantially longer than the length of the lower portion of the body 10 to permit the same to be anchored to mating felt surfaces 14 secured to the outside of the underlying end portions of said respective straps.

Main hanging straps 15 are provided which have relatively wide Velcro hook surfaces 15a and 15b, respectively, secured to the rear ends and to the front ends of said straps to permit the attachment points thereof to be universally adjusted to accomodate patients of all sizes and shapes. The back side of the straps have felt laminations applied thereto to mate with the Velcro hook surfaces on the underside of the circumferential straps 11a, b and c which reinforce the attachment of the straps 15 to the main body portion 10 of the vest assembly. The stretchable foam material of the body 10 is reinforced with a pair of bias tape elements 16 which extend generally vertically when in operative position and are positioned at the sides of the back panel 10c.

Figure 2:
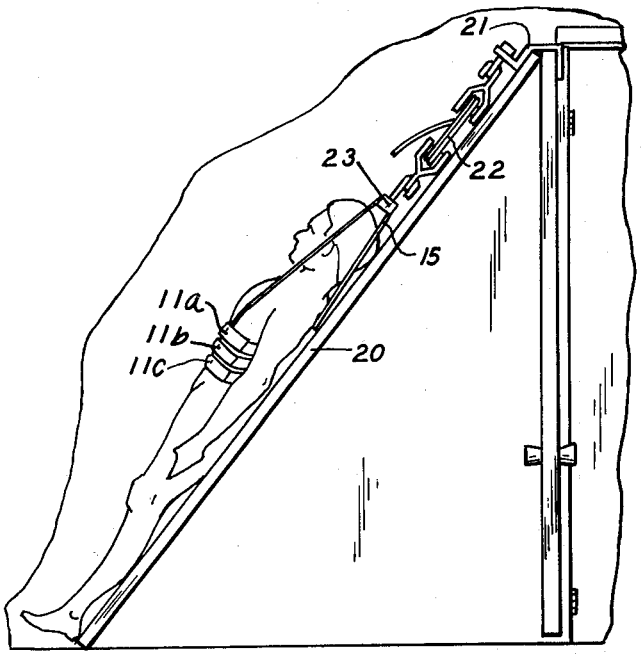
FIG. 2 is a side elevational view thereof.
Figure 5:
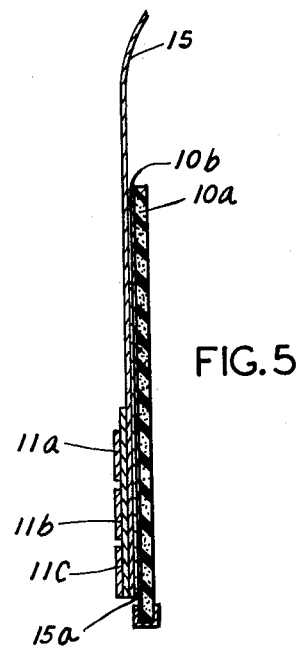
FIG. 5 is a fragmental sectional view taken substantially along the line 5—5 of FIG. 4.
Figure 3:
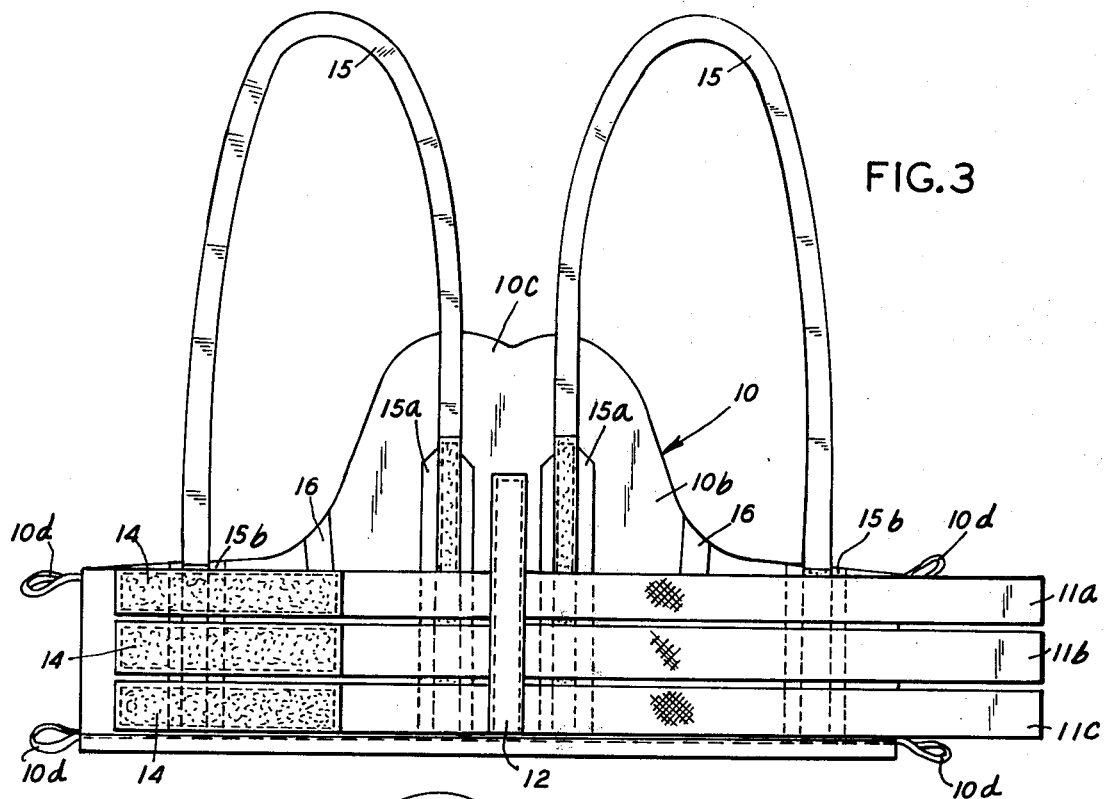
FIG. 3 is a rear elevational view of the brace, per se, laid out in open position.
Figure 4:
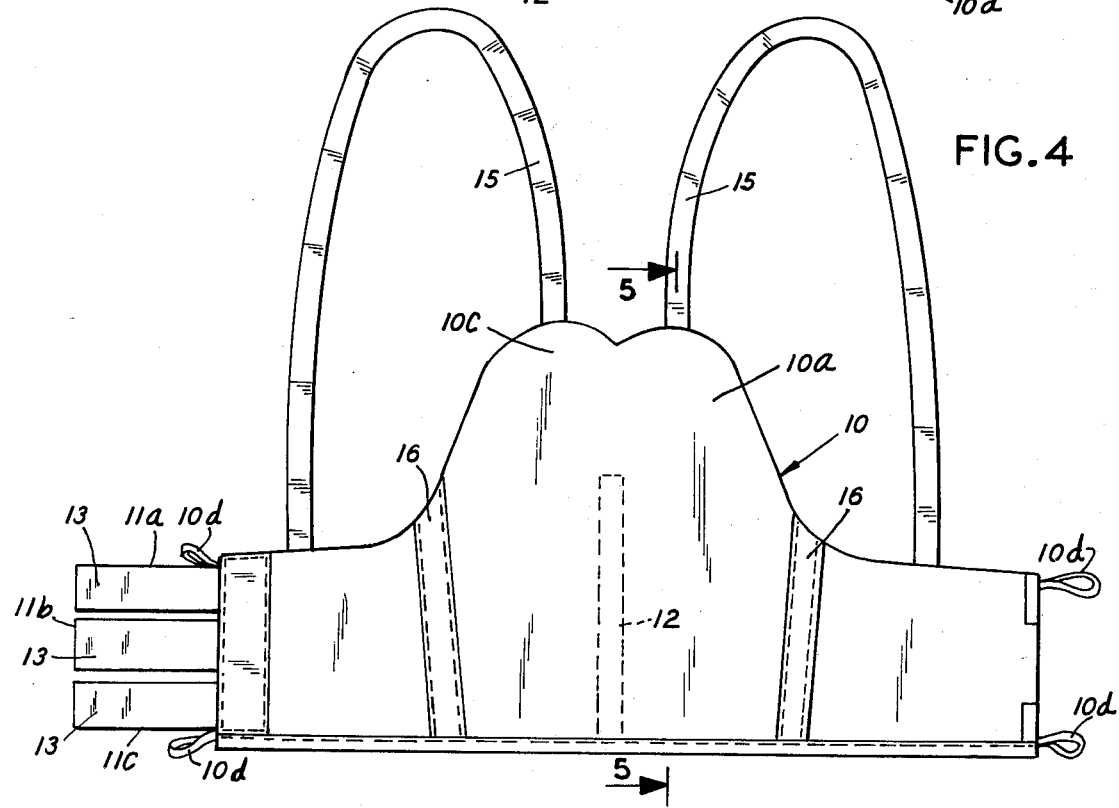
FIG. 4 is a front elevational view thereof.

The brace is initially applied to the patient by holding the vest body 10 around the lower rib cage in slightly stretched contour-conforming relation. This is accomplished by the use of the loops 10d. With the body held in stretched relation around the patient, the lower strap 11c is securely wrapped around the outside of the body portion 10 just below the lower ribs of the patient and the mating Velcro surfaces 13 and 14 of said lower strap are attached together. With the body portion still stretched around the lower rib cage, the other two straps 11a and 11b are similarly wrapped around the patient in secure, tight-fitting relation to positively hold the vest unit in place and provide the necessary comfortable and safe support for the patient's body in suspended traction-applying position, as shown in FIGS. 1 and 2. The use of an infinitely adjustable strap construction is very important to the safety and comfort of the patient.

The desired traction is then applied by supporting the patient at the desired angle from the supporting straps 15. In the form shown, this is accomplished by the use of an inclined slab or board member 20 which may be supported at the desired angle of inclination such as by brackets 21 hooked over the top of a door in the patient's home. Suitable means for hoisting the patient off the floor is illustrated, such as a block and tackle pulley system 22, which attaches the supporting straps 15 to the top of the slab 20 by means of a cross bar 23. The pulley system may have any suitable means for holding the patient in suspended relation with his feet a slight distance above the floor, such as a conventional locking cam arrangement (not shown) adjacent the upper pulley element. This permits the patient to suspend himself on the supporting slab after the brace is put on and also puts the patient in complete control of the length of time traction is being applied so that excessive pain can be avoided. Member 20 and other inclined supporting apparatus and their use with the traction harness are more fully described in the aforementioned application of Charles V. Burton, M.D.

Although certain materials have been specifically described in the above explanation of the preferred embodiment of this invention, it is important to note that other materials could be used which may afford the same advantages. Velcro attachment means have been used because they afford an essentially infinite number of attachment points, limited only by the length of the straps, which enables the patient himself to find the most comfortable adjustment without sacrificing safety.

It will of course be understood that various changes may be made in the form details, arrangement and proportions of the parts without departing from the scope of this invention which, generally stated, is as set forth in the appended claims.

What is claimed is:

1. An orthopedic lumbar traction brace, comprising:

(a) a torso surrounding vest having a layer uniformly made from stretchable material to conform to the contour of the lower rib cage and a portion of the torso therebelow;

(b) attachment means for securing the vest to a patient, the attachment means including a plurality of vertically spaced and circumferentially extending straps attached to the vest with each strap extending substantially completely around the vest, and further including means for tightening each strap in a circumferential direction with the lowermost strap being disposed immediately below the rib cage to substantially support the weight of the patient and the remaining straps being located around the rib cage to firmly grasp the rib cage and prevent movement of the vest relative thereto; and (c) support means connected to the vest for connecting the vest to means for holding the patient in a desired suspended position to apply gravity traction to the lumbar area of the spine.

2. An orthopedic lumbar traction brace as recited in claim 1, further including a hook and pile attachment between each strap and the vest along substantially the entire length of the strap.

3. An improved orthopedic lumbar traction brace as recited in claim 2, in which the support means comprises a plurality of hanging straps for connecting the vest to the holding means, and wherein each hanging strap has at least one end connected to the vest with that end having opposed faces, wherein each of the opposed faces of the one end of the hanging strap includes respectively a hook means and a pile means which define the components of a hook and pile attachment, whereby the one end of the hanging strap may be received between the vest and the circumferentially extending straps such that the hook and pile engagement between the straps and the vest coacts with the hook means and the pile means on the one end of the hanging strap to positively secure the hanging strap to the vest.

4. An orthopedic traction lumbar brace for connection to means for holding a patient in a desired suspended position to apply gravity traction to the lumbar area of the spine, which comprises:

(a) a torso sorrounding vest made from a stretchable material to conform to the contour of the lower rib cage and a portion of the torso therebelow, the vest having an outer surface which is formed with pile means which is adapted to coact with a hook means of a hook and pile attachment;

(b) attachment means for securing the vest to the patient for preventing movement of the vest after conformance thereof to the contour of the lower rib cage, the attachment means including a plurality of elongated circumferential straps secured to the vest and extending substantially around the entire outer surface thereof, wherein each of the circumferential straps includes means for tightening the strap around and below the lower rib cage to secure the vest thereto, and wherein the underside of each strap is formed with a hook means for securing the strap to the pile means on the outer surface of the vest along substantially the entire length of the strap; and (c) support means for connecting the vest to the holding means, wherein the support means comprises a plurality of U-shaped hanging straps secured to the vest, and wherein at least one end of the hanging strap is adjustable relative to the vest and includes two opposed faces which respectively have a hook means and a pile means, whereby the adjustable end of the hanging strap may be interposed between the vest and the circumferential straps such that the hook means on the hanging strap coacts with the pile means on the outer surface of the vest and the pile means on the opposed face of the hanging strap coacts with the hook means on the circumferential strap to allow the circumferential strap to reinforce the connection of the hanging strap to the vest.

5. A method of using an orthopedic lumbar traction brace which includes a torso surrounding vest made from a stretchable material and having a plurality of circumferentially extending straps secured thereto and extending around the vest for securing the vest to a patient, wherein each of the straps has means for tightening the strap in a circumferential direction, which comprises:

(a) placing the vest around the lower rib cage and a portion of the torso below the rib cage of the patient to allow the vest to conform thereto;

(b) securing the vest to the patient by tightening the lowermost strap of the vest beneath the rib cage to allow the weight to the patient to be borne thereon; and further tightening the remaining straps on the vest around the rib cage to allow the vest to grasp the rib cage to prevent upward movement of the vest thereon; and (c) connecting the vest to means for holding the patient in a desired hanging position to suspend the patient and apply gravity traction to the lumbar area of the spine.

6. An orthopedic lumbar traction brace as recited in claim 1 or claim 4, wherein said torso surrounding vest layer is made from a padded material.

* * * * *